US011820984B2

(12) United States Patent
Lee et al.

(10) Patent No.: US 11,820,984 B2
(45) Date of Patent: Nov. 21, 2023

(54) DOUBLE-HELIX OLIGONUCLEOTIDE CONSTRUCT COMPRISING DOUBLE-STRANDED MIRNA AND USE THEREOF

(71) Applicant: BIONEER CORPORATION, Daejeon (KR)

(72) Inventors: Taewoo Lee, Seoul (KR); Jiwon Ryu, Daejeon (KR); Eun Ji Im, Seoul (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 16/963,998

(22) PCT Filed: Jan. 29, 2019

(86) PCT No.: PCT/KR2019/001187
§ 371 (c)(1),
(2) Date: Jul. 22, 2020

(87) PCT Pub. No.: WO2019/151738
PCT Pub. Date: Aug. 8, 2019

(65) Prior Publication Data
US 2021/0032628 A1 Feb. 4, 2021

(30) Foreign Application Priority Data

Jan. 30, 2018 (KR) .................. 10-2018-0011141
Jan. 9, 2019 (KR) .................. 10-2019-0002800

(51) Int. Cl.
*C12N 15/113* (2010.01)
*A61P 35/00* (2006.01)

(52) U.S. Cl.
CPC .......... *C12N 15/1136* (2013.01); *A61P 35/00* (2018.01); *C12N 2310/141* (2013.01); *C12N 2310/50* (2013.01)

(58) Field of Classification Search
CPC .......... C12N 15/1136; C12N 2310/141; C12N 2310/50; A61P 35/00
See application file for complete search history.

(56) References Cited

U.S. PATENT DOCUMENTS

| 2014/0147454 A1 | 5/2014 | Chakraborty et al. |
| 2014/0200261 A1 | 7/2014 | Hoge et al. |
| 2016/0122764 A1* | 5/2016 | Chae ............ A61P 11/10 536/24.5 |

FOREIGN PATENT DOCUMENTS

| EP | 2796150 A1 | 10/2014 |
| EP | 2805713 A1 | 11/2014 |
| JP | 2011526548 A | 10/2011 |
| JP | 2016525346 A | 8/2016 |
| KR | 10-0883471 B1 | 2/2009 |
| KR | 1020090055623 A | 6/2009 |
| KR | 1020090057383 A | 6/2009 |
| KR | 1020100123214 A | 11/2010 |
| KR | 10-1224828 B1 | 1/2013 |
| KR | 1020160033125 A | 3/2016 |
| KR | 1020160103949 A | 9/2016 |
| WO | WO2008154333 A2 | 12/2008 |
| WO | 2014164253 A1 | 10/2014 |
| WO | WO-2016137235 A2 * | 9/2016 ......... A61K 31/7105 |

OTHER PUBLICATIONS

Mo et al. (OnocoTargets and Therapy (2014) 7:895-900) (Year: 2014).*
Wang et al. Investigational New Drugs vol. 47:1127-1134 (published Feb. 9, 2019) (Year: 2019).*
Haga, C.L., et al., "MicroRNAs in the Imprinted DLK1-DIO3 Region Repress the Epithelial-to-Mesenchymal Transition by Targeting the TWIST1 Protein Signaling Network", The Journal of Biological Chemistry, 2012, pp. 42695-42707, vol. 287, No. 51, Publisher: American Society for Biochemistry and Molecular Biology.
He, Q., et al., "circ-SHKBP1 Regulates the Angiogenesis of U87 Glioma-Exposed Endothelial Cells through miR-544a/FOXP1 and miR-379/FOXP2 Pathways", Molecular Therapy Nucleic Acids, 2017, pp. 331-348, vol. 10, Publisher: American Society of Gene & Cell Therapy.
Jin, S., et al., "MicroRNA-544 inhibits glioma proliferation, invasion and migration but induces cell apoptosis by targeting PARK7", Am J Transl Res, 2016, pp. 1826-1837, vol. 8, No. 4.
Mao, L., et al., "Transcription factor KLF4 regulates microRNA-544 that targets YWHAZ in cervical cancer", Am J Cancer Res, 2015, pp. 1939-1953, vol. 5, No. 6.
Zhu, Z., et al., "MicroRNA-544 down-regulates both Bc16 and Stat3 to inhibit tumor growth of human triple negative breast cancer", Biol. Chem, 2016, pp. 1087-1095, vol. 397, No. 10.
Agostini, M., et al., "MiR-34: from bench to bedside", "Oncotarget", Apr. 21, 2014, pp. 872-881, vol. 5, No. 4.
Bartel, D. P., "MicroRNAs: Target Recognition and Regulatory Functions", "Cell", Jan. 23, 2009, pp. 215-233, vol. 136.
Brodersen, P., et al., "Revisiting the principles of microRNA target recognition and mode of action", "Nature Reviews", Feb. 2009, pp. 141-148, vol. 10.
Burnett, J. C., et al., "RNA-Based Therapeutics: Current Progress and Future Prospects", "Chemistry & Biology", Jan. 27, 2012, pp. 60-71, vol. 19.
Carthew, R. W., et al., "Origins and Mechanisms of miRNAs and siRNAs", "Cell", Feb. 20, 2009, pp. 642-655, vol. 136.
Chang, T.-C., et al., "Transactivation of miR-34a by p53 broadly influences gene expression and promotes apoptosis", "Molecular Cell", Jun. 8, 2007, pp. 745-752, vol. 26, No. 5.

(Continued)

*Primary Examiner* — J. E. Angell
(74) *Attorney, Agent, or Firm* — HULTQUIST, PLLC; Steven J. Hultquist

(57) ABSTRACT

The present invention relates to a double-helix oligonucleotide construct comprising a double-stranded miRNA and a composition for preventing or treating cancer comprising the same. More particularly, the present invention relates to a double-helix oligonucleotide construct comprising miR-544a characterized by a method that effectively inhibits the proliferation of cancer cells or induces a voluntary death of cancer cells, and an anticancer composition comprising the construct.

14 Claims, 10 Drawing Sheets

Specification includes a Sequence Listing.

(56) References Cited

OTHER PUBLICATIONS

Chu, C.-Y., et al., "Potent RNAi by short RNA triggers", "RNA", Jul. 24, 2008, pp. 1714-1719, vol. 24.

Dangwal, S., et al., "MicroRNA Therapeutics in Cardiovascular Disease Models", "Annual Review of Pharmacology and Toxicology", Sep. 17, 2013, p. 10.1-10.19, vol. 54.

Hermeking, H., "The miR-34 family in cancer and apoptosis", "Cell Death and Differentiation", May 22, 2009, pp. 193-199, vol. 17.

Iorns, E., et al., "Utilizing RNA interference to enhance cancer drug discovery", "Nature Reviews", Jul. 2007, pp. 556-568, vol. 6.

Jackson, A. L., et al., "Expression profiling reveals off-target gene regulation by RNAi", "Nature Biotechnology", Jun. 2003, pp. 635-637, vol. 21, No. 6.

Jackson, A. L., et al., "Position-specific chemical modification of siRNAs reduces off-target transcript silencing", "RNA", 2006, pp. 1197-1205, vol. 12.

Jackson, A. L., et al., "Widespread siRNA off-target transcript silencing mediated by seed region sequence complementarity", "RNA", 2006, pp. 1179-1187, vol. 12.

Kim, S., et al., "Local and systemic delivery of VEGF siRNA using polyelectrolyte complex micelles for effective treatment of cancer", "Journal of Controlled Release", Mar. 14, 2008, pp. 107-116, vol. 129, No. 2.

Landi, D., et al., "Role of variations within microRNA-binding sites in cancer", "Mutagenesis", 2012, pp. 205-210, vol. 27, No. 2.

MacFarlane, L.-A., et al., "MicroRNA: Biogenesis, Function and Role in Cancer", "Current Genomics", 2010, pp. 537-561, vol. 11.

Malone, C. D., et al., "Small RNAs as Guardians of the Genome", "Cell", 2009, pp. 656-668, vol. 136.

Mittal, V., "Improving the Efficiency of RNA Interference in Mammals", "Nature Reviews", May 2004, pp. 355-365, vol. 5.

Mo, X., et al., "MiR-544a Promotes the Invasion of Lung Cancer Cells by Targeting Cadherina I in Vitro", "OncoTargets and Therapy", 2014, pp. 895-900, vol. 7.

NCBI, "Canis Lupus Familiaris microRNA 544 (MIR544), microRNA", "NCBI Reference NR_049499.1", Oct. 24, 2017, pp. 1-3.

Nicoloso, M. S., et al., "MicroRNAs—the micro steering wheel of tumour metastases", "Nature Reviews", Apr. 2009, pp. 293-302, vol. 9.

Nielsen, C. B., et al., "Determinants of targeting by endogenous and exogenous microRNAs and siRNAs", "RNA", 2007, pp. 1894-1910, vol. 13.

Peek, A. S., et al., "Design of active small interfering RNAs", "Current Opinion in Molecular Therapeutics", 2007, pp. 110-118, vol. 9, No. 2.

Potenza, N., et al., "Human MiR-544a Modulates SELK Expression in Hepatocarcinoma Cell Lines", "PLOS One", Jun. 8, 2016, pp. 1-13, e0156908, vol. 11, No. 6.

Reynolds, A., et al., "Rational siRNA design for RNA interference", "Nature Biotechnology", Mar. 2004, pp. 326-330, vol. 22, No. 3.

Soutschek, J., et al., "Therapeutic silencing of an endogenous gene by systemic administration of modified siRNAs", "Nature", Nov. 11, 2004, pp. 173-178, vol. 432, No. 7014.

Tomari, Y., et al., "Perspective: machines for RNAi", "Genes & Development", 2005, pp. 517-529, vol. 19.

Van Rooij, E., et al., "Developing MicroRNA Therapeutics", "Circulation Research", 2012, pp. 496-507, vol. 110.

Wiggins, J. F., et al., "Development of a Lung Cancer Therapeutic Based on the Tumor Suppressor MicroRNA-34". "Cancer Research", Jul. 15, 2010, pp. 5923-5930, vol. 70, No. 14.

Office Action issued in Chinese Patent Application No. 201980016085.3 dated Mar. 30, 2023.

English Translation of Office Action issued in Chinese Patent Application No. 201980016085.3 dated Mar. 30, 2023.

Search Report issued in Chinese Patent Application No. 201980016085.3 dated Mar. 30, 2023.

Li, H., et al., "Expression of GSK3, an inhibitory factor of the Wnt signaling pathway, in non-small cell lung cancer regulated by miR-544a", Chinese Journal of Clinical Laboatory Science, 2013, pp. 761-764, vol. 10, Publisher: China/Asia on Demand.

Mo, X-M, et al., "Downregulation of GSK3 by miR-544a to maintain self-renewal ability of lung cancer stem cells", Oncology Letters, 2014, pp. 1731-1734, vol. 8.

English Translation of Office Action Issued in Chinese Patent Application No. 201980016085.3 dated Aug. 23, 2023.

Office Action Issued in Chinese Patent Application No. 201980016085.3 dated Aug. 23, 2023.

Search Report Issued in Chinese Patent Application No. 201980016085.3 dated Aug. 23, 2023.

\* cited by examiner

DOUBLE-HELIX OLIGONUCLEOTIDE CONSTRUCT COMPRISING DOUBLE-STRANDED MIRNA AND USE THEREOF

CROSS-REFERENCE TO RELATED APPLICATIONS

This application is a U.S. national phase under the provisions of 35 U.S.C. § 371 of International Patent Application No. PCT/KR2019/001187 filed Jan. 29, 2019, which in turn claims priority under 35 U.S.C. § 119 of Korean Patent Application No. 10-2018-0011141 filed Jan. 30, 2018 and priority under 35 U.S.C. § 119 of Korean Patent Application No. 10-2019-0002800 filed Jan. 9, 2019. The disclosures of such International Patent Application No. PCT/KR2019/001187, Korean Patent Application No. 10-2018-0011141, and Korean Patent Application No. 10-2019-0002800 are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "526_SeqListing_ST25.txt" created on Jul. 22, 2020 and is 757 bytes in size. The sequence listing contained in this .txt file is part of the specification and is hereby incorporated by reference herein in its entirety.

TECHNICAL FIELD

The present invention relates to a double-stranded oligonucleotide structure comprising double-stranded miRNA, and a composition for cancer prevention or treatment comprising the same. More specifically, the present invention relates to a double-stranded oligonucleotide structure comprising miR-544a, which effectively inhibits cancer cell proliferation or induces cancer cell apoptosis, and an anticancer composition comprising the structure.

BACKGROUND ART

As effective and traditional methods for treating diseases caused by abnormalities in gene control, typically diseases referred to as cancers, methods of removing tumors by surgical excision have been used. However, where primary cancer is metastasized to other organs, surgical excision is impossible and anticancer chemotherapy has been used. As anticancer agents for chemotherapy, monomolecular compounds synthesized by organic or inorganic methods have mainly been used. Such anticancer drugs have been developed and used against cancer diseases in order mainly to effectively target proteins that disturb signaling pathways by overexpression of phosphorylation activator proteins included in the signaling pathways, thereby inhibiting the activity of the proteins.

In the recent trend of anticancer drug development, targeted therapeutic agents have been developed, which target cancer-causing driver mutations and selectively inhibit the activity of proteins generated by the driver mutations. 85 to 90% of lung cancer is non-small cell lung cancer which can be subdivided into squamous cell carcinoma and adenocarcinoma. As major genetic mutations impacting survival rates of adenocarcinoma, KRAS mutations accounting for about 30% and EGFR mutations accounting for 15% are known.

In particular, targeted therapeutic agents that target mutated EGFR proteins have been developed and used clinically, and examples thereof include erlotinib (trade name: Tarceva) and gefitinib (trade name: Iressa). Although these targeted therapeutic agents yield high response rates from lung cancer patients with EGFR mutations, it has been reported that resistance to these drugs is induced within a year in most cases. The resistance has been reported to be caused by either T790M mutation in EGFR protein in addition to existing EGFR mutations, or mutations in genes such as RAF and PI3K included downstream of the EGFR signaling pathway. Lung cancer therapeutic drugs comprising such monomolecule have fatal limitations such as induction of drug resistance.

Development of therapeutic drugs to replace traditional chemotherapies has been attempted in various ways. One of such attempts is the use of small interfering RNA (hereinafter referred to as siRNA) (Iorns, E et al., Nat Rev Drug Discov Vol. 6, pp. 556-68. 2007.). siRNA is a single-stranded RNA consisting of 16 to 27 nucleotides and serves as one component of a ribonucleoprotein complex known as an RNA Induced Silencing Complex (RISC) in cells (Tomari, Y et al., Genes Dev Vol. 19, pp. 517-29, 2005, Chu, C. Y et al., RNA Vol. 14, pp. 1714-9, 2008, Mittal, V. Nat Rev Genet Vol. 5, pp. 355-65, 2004, Reynolds, A. et al. Nat Biotechnol Vol. 22, pp. 326-30. 2004). The RISC functions as RNA scissors to cleave messenger RNA (hereinafter referred to as mRNA) to thereby inhibit the production of protein from mRNA. siRNA contained in the RISC may bind to mRNA having a sequence complementary to the siRNA sequence to form double-stranded RNA, and the RISC may act as RNA scissors to cleave target mRNA so that the mRNA can no longer function as a template that repeatedly produces protein.

The siRNA-based anticancer drugs as described above are considered more advanced than monomolecular anticancer drugs in that they cleave mRNA before protein production and use RNA and the intracellular RISC pathway. However, there is a side effect that cannot be solved even by the siRNA-based technology, this side effect is a phenomenon known as the off-target effect. (Jackson, A. L. et al., Rna Vol. 12, pp. 1179-87, 2006, Jackson, A. L. et al., Rna Vol. 12, pp. 1197-205, 2006, Jackson, A. L. et al., Nat Biotechnol Vol. 21, pp. 635-7, 2003, Nielsen, C. B. et al., Rna Vol. 13, pp. 1894-910, 2007, Peek, A. S. & Behlke, M. A. Curr Opin Mol Ther Vol. 9, pp. 110-8, 2007.). As described above, siRNA acts to cleave mRNA having a sequence complementary to the siRNA sequence. However, siRNA may also bind to and cleave non-target mRNA which is not complementary to the entire sequence of the siRNA, but is only complementary to a portion of the siRNA sequence. This phenomenon is known as the off-target effect.

To overcome the above-described technical disadvantage of siRNA-based anticancer drugs, studies on the use of microRNA (hereinafter referred to as "miRNA") as therapeutic agents are underway (Agostini, M. & Knight, R. A. Oncotarget Vol. 5, pp. 872-81, 2014, van Rooij, E. et al., Circulation Research Vol. 110, pp. 496-507, 2012, Burnett, J. C. & Rossi, J. J. Chem Biol Vol. 19, pp. 60-71, 2012, Dangwal, S. & Thum, T. Annu Rev Pharmacol Toxicol Vol. 54, pp. 185-203, 2014.). miRNA is RNA consisting of 16 to 27 nucleotides and is classified as protein non-coding RNA against a messenger RNA (mRNA) that is translated into protein (Carthew, R. W. & Sontheimer, E. J. Cell Vol. 136, pp. 642-55, 2009, MacFarlane, L.-A. & Murphy, P. R. Current Genomics Vol. 11, pp. 537-561, 2010, Bartel, D. P. Cell Vol. 136, pp. 215-33, 2009.). miRNA is found in the genome of higher animal and plant cells, and is known to play a key role in regulating cell metabolism and functions, including cell production, growth, differentiation and death. Until now, about 2000 kinds of miRNA have been found in the human genome, and the functions of a considerable number of the miRNAs are not yet known.

miRNA is transcribed from the genome into RNA by RNA polymerase known as Pol II, and the initial length of the miRNA is various without being specified (Carthew, R. W. & Sontheimer, E. J. Cell Vol. 136, pp. 642-55, 2009, Brodersen, P. & Voinnet, O. Nat Rev Mol Cell Biol Vol. 10, pp. 141-148, 2009.). This is attributable to the positional variety of miRNA in the genome. This is because miRNA is produced in various ways, including the case in which miRNA located in an intron (mRNA non-coding region) is transcribed at the same time point as mRNA production and in the case in which miRNA located in the intergenic region of the genome is transcribed individually (Malone, C. D. & Hannon, G. J. Cell Vol. 136, pp. 656-68, 2009.). miRNA produced in the initial stage as described above is known as primary microRNA (miR). Primary miR is processed into precursor miR (precursor miRNA, or pre-miR) by, for example, RNase known as intranuclear Drosha (Bartel, D. P. Cell Vol. 136, pp. 215-33, 2009.). Pre-miR has an RNA hairpin structure and consists of about 70 to 80 nucleotides. Pre-miR in the cellular nucleus is transported from the nucleus to the cytosol by exportin protein or the like, and is further processed in the cytosol by another RNase known as Dicer to thereby produce double-stranded mature microRNA (hereinafter, miR described without a qualifier means mature miR) consisting of 16 to 27 nucleotides. One RNA strand of double-stranded miR is selected, activated by binding to the ribonucleoprotein complex RISC, and binds to target mRNA based on the sequence of miR.

In general, mRNA can be broadly divided into three regions based on whether or not these regions are involved in protein coding: a coding region containing protein coding translation information, and 5'-UTR (UnTranslated Region) and 3'-UTR which have no protein coding information. While siRNA that induces cleavage of target mRNA having a sequence complementary thereto acts regardless of the 5'-UTR, 3'-UTR and coding region of mRNA, miR binds mainly to the 3'-UTR (Carthew, R. W. & Sontheimer, E. J. Cell Vol. 136, pp. 642-55, 2009, Bartel, D. P. Cell Vol. 136, pp. 215-33, 2009.).

In addition to the difference in the position of binding to mRNA, the characteristic difference between siRNA and miRNA is that siRNA binds mainly to mRNA having a sequence complementary to the entire sequence of siRNA, whereas miRNA recognizes target mRNA, mainly through a seed region sequence having a limited length located 2 to 8 nucleotides from the 5' end of the miRNA. Thus, even when the entire sequence of miRNA is not completely complementary to the sequence of a target sequence and contains a non-complementary sequence portion, the activity of the miRNA is not affected by the non-complementary sequence portion (Bartel, D. P. Cell Vol. 136, pp. 215-33, 2009.). Since the seed region is 6 to 8 nucleotides in length, there are various kinds of mRNAs whose 3' UTR has a sequence complementary to the seed region, and for this region, several kinds of mRNAs can be simultaneously controlled using one kind of miRNA. This nature of miRNA enables the miRNA to function as an efficient regulator in the control of many cellular physiological aspects, including cell division, growth, differentiation and death. Furthermore, the function of miRNA as a regulator provides an advantage in achieving effective anticancer effects. This is because miRNA can inhibit expression of a number of oncogenes at the same time, whereas siRNA aims to inhibit expression of a single gene.

The 3' UTR of many mRNAs contains a portion to which one or more miRNAs can bind. According to bioinformatics calculation, it is known that about 30% of all mRNAs are regulated by miRNA with protein production.

The fact that miRNA acts as a major regulator in signaling pathways can be seen from the fact that miRNA plays an important role in major diseases, including cancer (MacFarlane, L.-A. & Murphy, P. R. Current Genomics Vol. 11, pp. 537-561. 2010, Malone, C. D. & Hannon, G. J. Cell Vol. 136, pp. 656-68. 2009, Nicoloso, M. S. et al., Nat Rev Cancer Vol. 9, pp. 293-302. 2009, Landi, D. et al., Mutagenesis Vol. 27, pp. 205-10. 2012.). In fact, several studies revealed that expression patterns of miRNAs in cancer cells greatly differ from expression patterns of miRNAs in normal cells. In addition, it is known that expression patterns of miRNAs greatly differ depending on primary organs in which cancer occurred. Specifically, various cancers, including lung cancer, liver cancer, skin cancer and blood cancer, show characteristic miRNA expression patterns according to the primary organs, indicating that miRNA plays an important role in cancer biology. In particular, it is known that the expression levels of miRNA in cancer cells are generally lower than their expression levels in normal cells.

Based on the deep connection between miRNA and cancer, it has recently been attempted to use miRNAs as anticancer therapeutic agents. For example, miRNA, named "miR-34a", is under clinical trials to verify its ability to inhibit cancer cell proliferation and induce cancer cell apoptosis (Wiggins, J. F. et al. Cancer Res Vol. 70, pp. 5923-30. 2010, WO2008/154333, Hermeking, H. Cell Death Differ Vol. 17, pp. 193-9. 2010, Chang, T. C. et al. Mol Cell Vol. 26, pp. 745-52. 2007.).

The use of miRNA as an anticancer agent requires an effective method for delivering miRNA, injected from outside the body, to pathological tissues without being degraded in vivo. To this end, an RNA oligonucleotide structure comprising a miRNA sequence may be used. It is known that the high in vivo efficiency of an RNA oligo can be induced by linking a chemical substance, etc., to the end of the RNA oligo to have enhanced pharmacokinetic characteristics (Soutschek. J. et al., Nature Vol. 432 Issue. 7014 pp. 173-8, 2004). At this time, the stability of the RNA oligo varies depending on the nature of the chemical substance linked to the end of the sense (passenger) or antisense (guide) strand of the RNA oligo. For example, an RNA oligo conjugated to a polymer compound such as polyethylene glycol (PEG) interacts with an anionic phosphate group in the presence of a cationic substance to form a complex which acts as a carrier with improved oligo stability (Kim S H et al., J Control Release Vol. 129(2) pp. 107-16, 2008). In particular, micelles consisting of polymer complexes have an extremely small size and a very uniform distribution and are spontaneously formed, compared to microspheres or nanoparticles which are other systems used as drug delivery carriers. Thus, these micelles have an advantage in that it is easy to control the quality of formulation and ensure reproducibility.

In addition, in order to improve the intracellular delivery efficiency of an RNA oligo, technology was developed which ensures the stability of the oligo and allows efficient cell membrane penetration of the oligo through an oligo conjugate obtained by conjugating a biocompatible and hydrophilic polymer (e.g., polyethylene glycol (PEG)) to the RNA oligo by a simple covalent bond or a linker-mediated covalent bond (Korean Patent No. 10-0883471). However, the oligo conjugate obtained by chemical modification of the oligo and conjugation of polyethylene glycol (PEG) (PEGylation) to the oligo still have disadvantages in that the oligo conjugate has low stability in vivo and the delivery thereof to a target organ is not smooth. In order to solve these disadvantages, a double-stranded oligonucleotide structure was developed in which hydrophilic and hydrophobic compounds are bound to a double-stranded oligo RNA. The structure forms self-assembled nanoparticles, referred to as SAMiRNA™ (self-assembled micelle inhibitory RNA), by the hydrophobic interaction of the hydrophobic compound moieties (see Korean Patent No. 10-1224828). The SAMiRNA™ technology has an advantage over conventional delivery technologies in that homogenous nanoparticles with a very small size can be obtained.

Under this technical background, the present inventors have made efforts to discover a miRNA having an excellent ability to inhibit cancer cell proliferation and induce cancer cell apoptosis, and as a result, have discovered miR-544a having excellent anticancer efficacy and have found that a double-stranded oligonucleotide structure comprising the same exhibits an anticancer effect by effectively inhibiting expression of a number of genes known as oncogenes, thereby completing the present invention.

The above information disclosed in this Background section is only for enhancement of understanding of the background of the present invention. Therefore, it may not contain information that forms conventional art that is already known in the art to which the present invention pertains.

SUMMARY OF THE INVENTION

It is an object of the present invention to provide a double-stranded oligonucleotide structure comprising miRNA, which can overcome drug resistance of lung cancer cells having EGFR mutation to erlotinib (which is used as a lung cancer therapeutic agent) and has an excellent ability to inhibit cancer cell proliferation and induce cancer cell apoptosis, and a composition for cancer prevention or treatment comprising the same as an active ingredient.

To achieve the above object, the present invention provides a double-stranded oligonucleotide structure comprising a structure of the following structural formula (1):

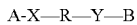 (1)

wherein A represents a hydrophilic compound; B represents a hydrophobic compound; X and Y each independently represent a simple covalent bond or a linker-mediated covalent bond; and R represents an miR-544a sequence.

The present invention also provides a composition for cancer prevention or treatment comprising the oligonucleotide structure.

The present invention also provides a method for cancer prevention or treatment comprising a step of administering the oligonucleotide structure.

The present invention also provides the oligonucleotide structure for use in the cancer prevention or treatment.

The present invention provides the use of the oligonucleotide structure in the manufacture of a medicament for cancer prevention or treatment.

BRIEF DESCRIPTION OF DRAWINGS

FIG. 9 shows the cell viability of lung cancer cell lines having EGFR mutation after treatment with erlotinib and miR544a.

DETAILED DESCRIPTION AND PREFERRED EMBODIMENTS OF THE INVENTION

Unless otherwise defined, all the technical and scientific terms used in the present specification have the same meanings as commonly understood by those skilled in the art to which the present disclosure pertains. In general, the nomenclature used in the present specification is well known and commonly used in the art.

In the present invention, a miRNA, which exhibits an excellent effect by inhibiting the EGFR signaling pathway in lung cancer cells having EGFR mutation and inhibiting the proliferation of the cells, was discovered and the anticancer effect of the miRNA was evaluated.

Figure 1:
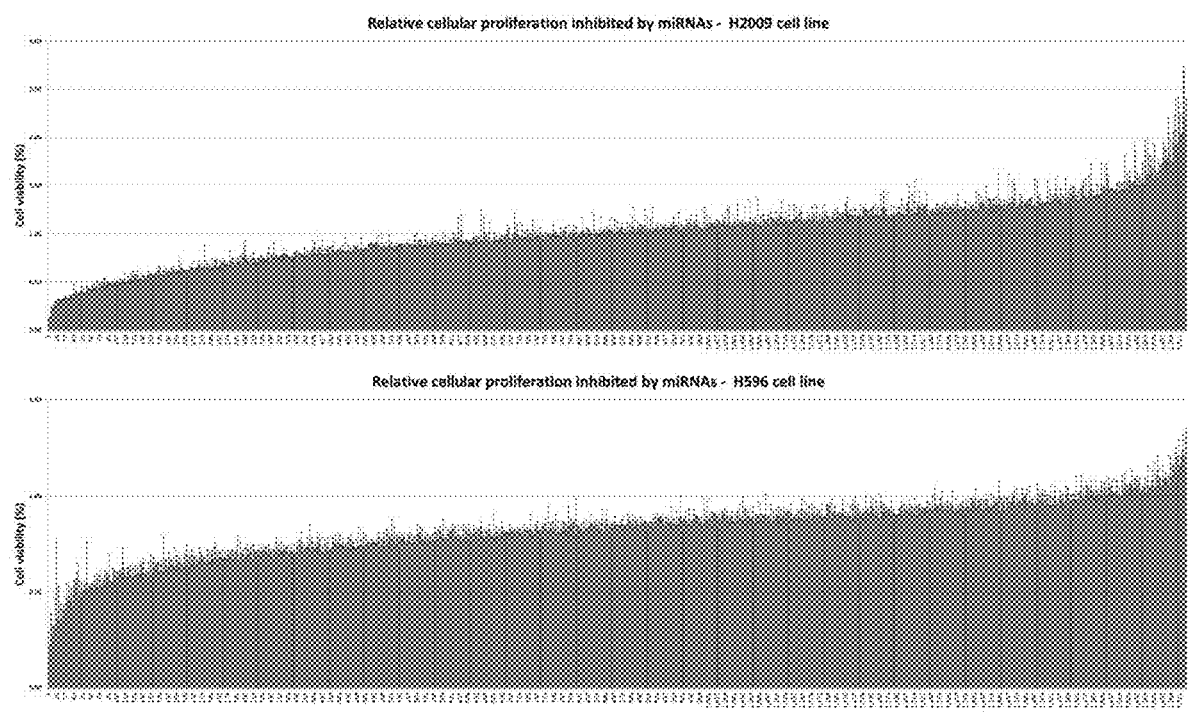
FIGS. 1 to 4 show the results of miRNA library screening obtained by transfecting eight kinds of lung cancer cell lines with a miRNA library and measuring the inhibition of proliferation of the cells.
Figure 2:
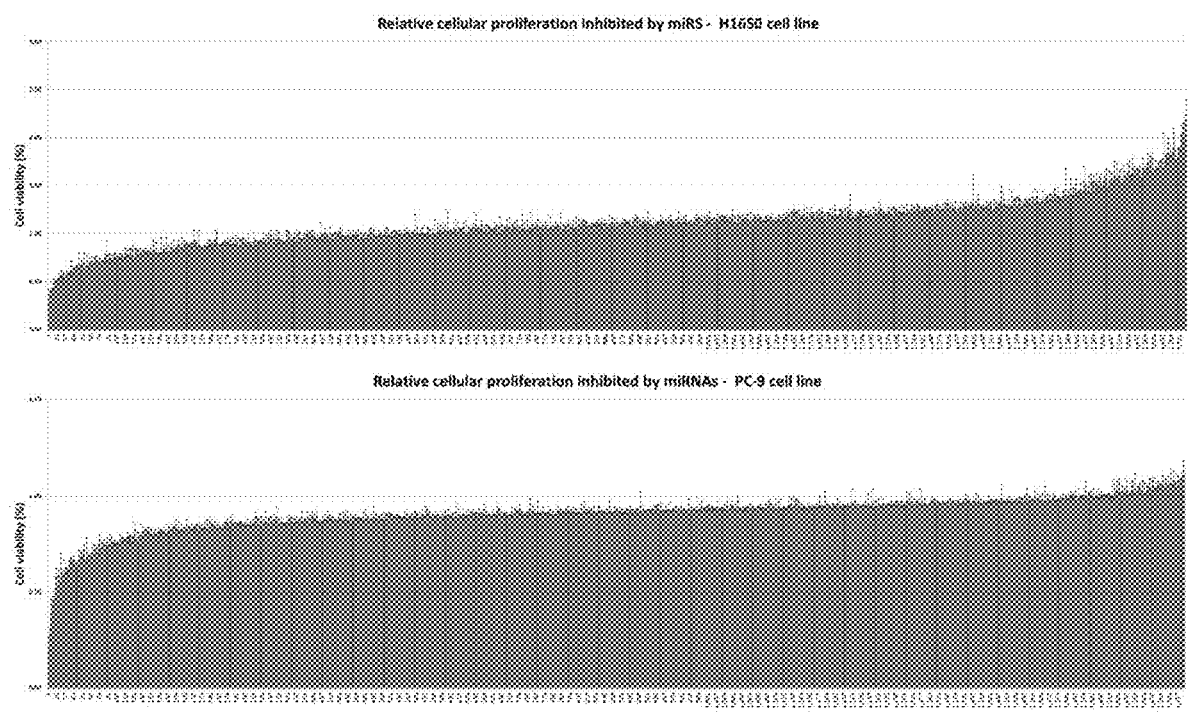
Figure 3:
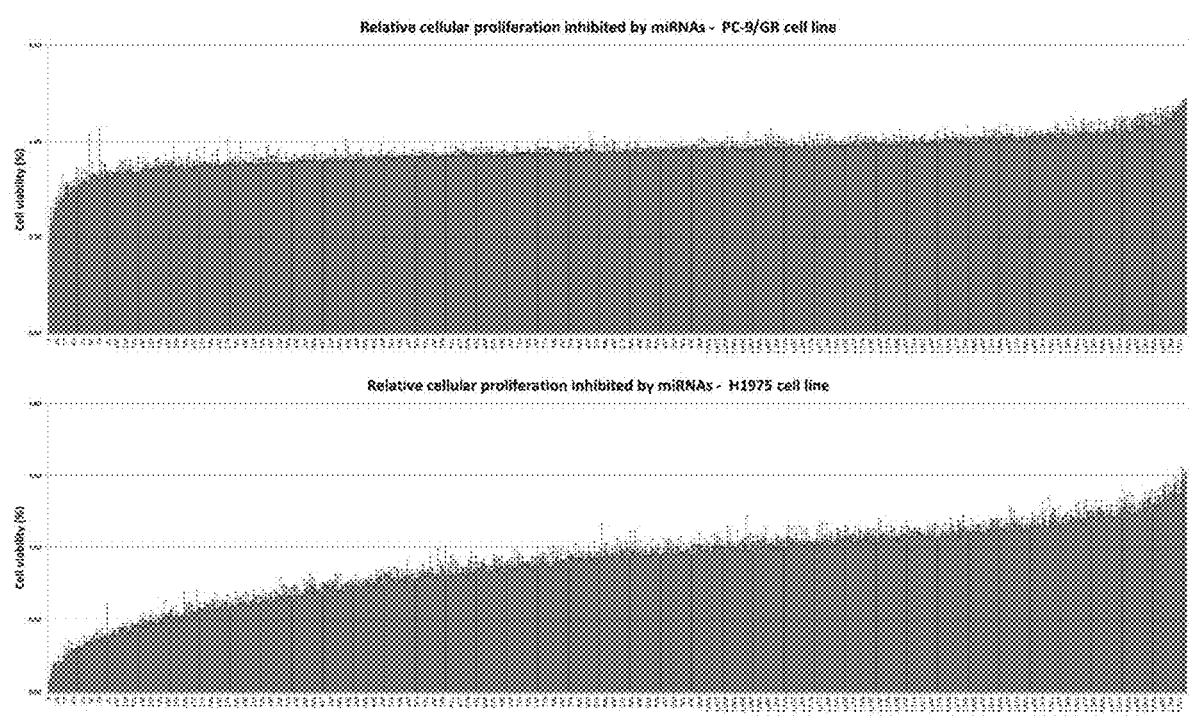
Figure 4:
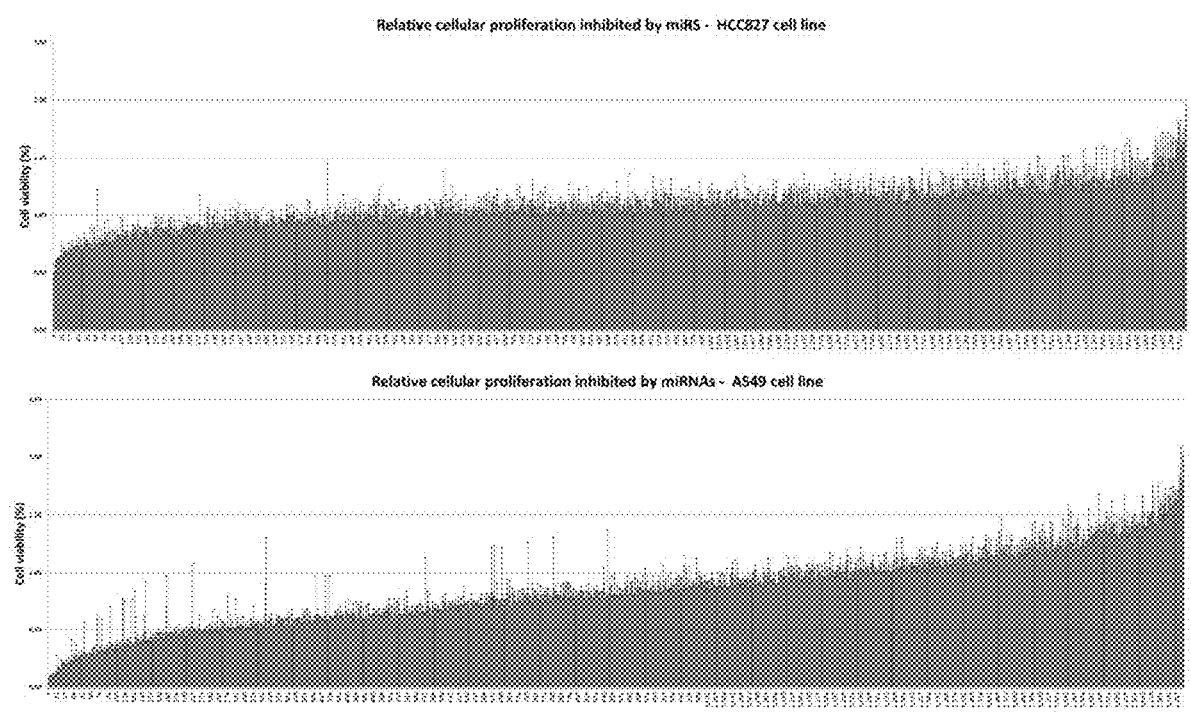
Figure 5:
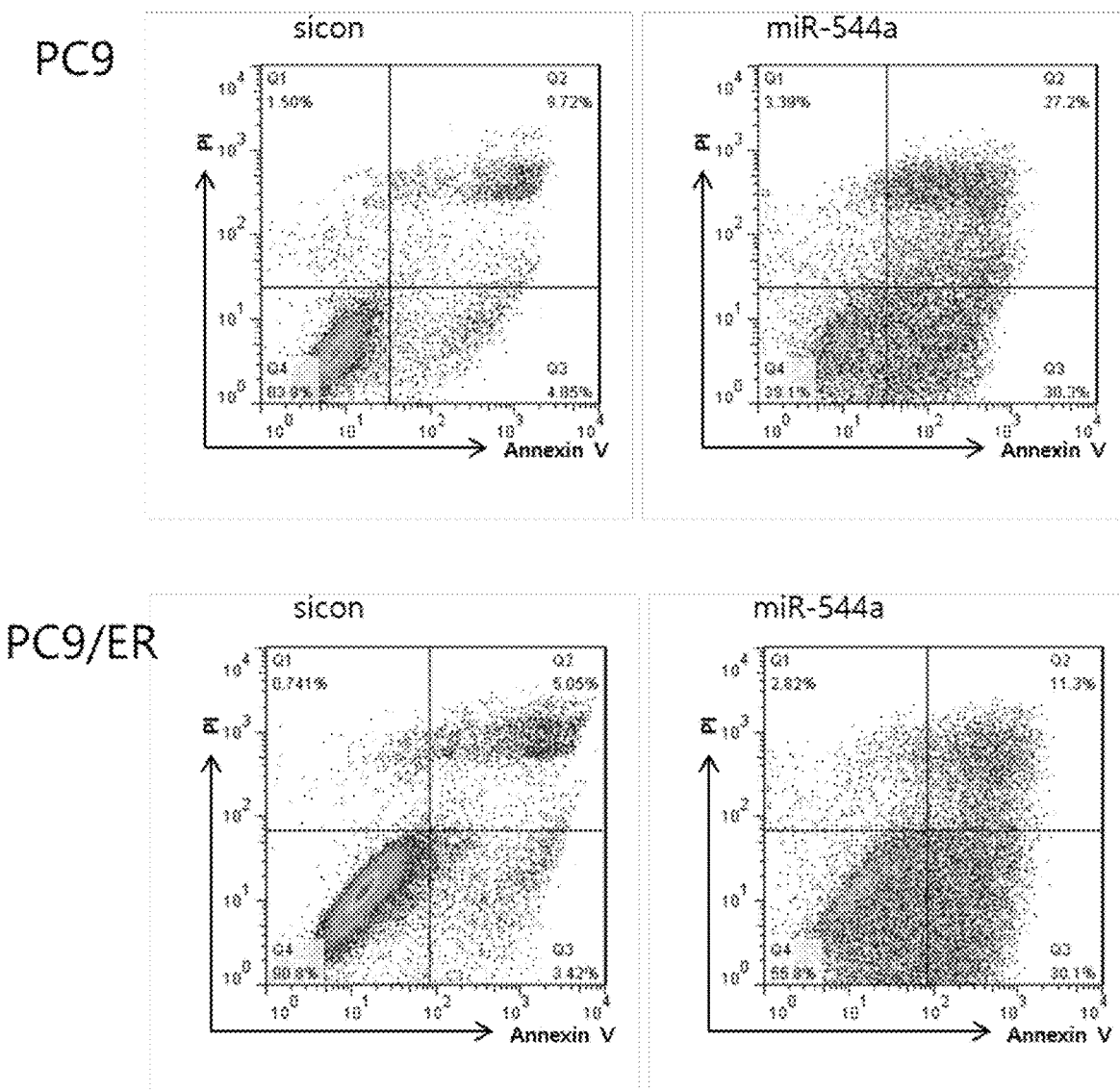
FIG. 5 shows the apoptosis-inducing effect of miR-544a on the PC9 and PC9/ER cell lines.
Figure 6:
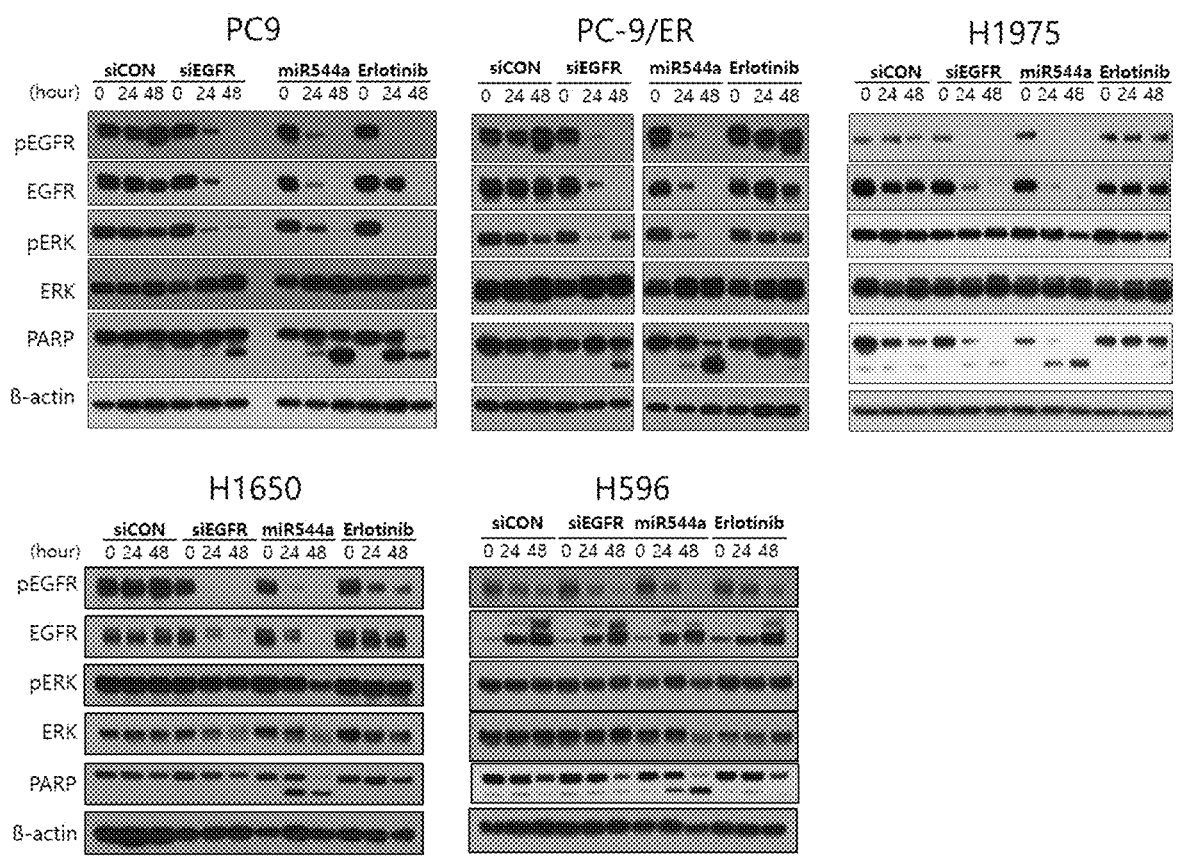
FIG. 6 shows the results of Western blot analysis performed to measure the effect of miR-544a on the regulation of proteins involved in the EGFR signaling pathway.
Figure 9:
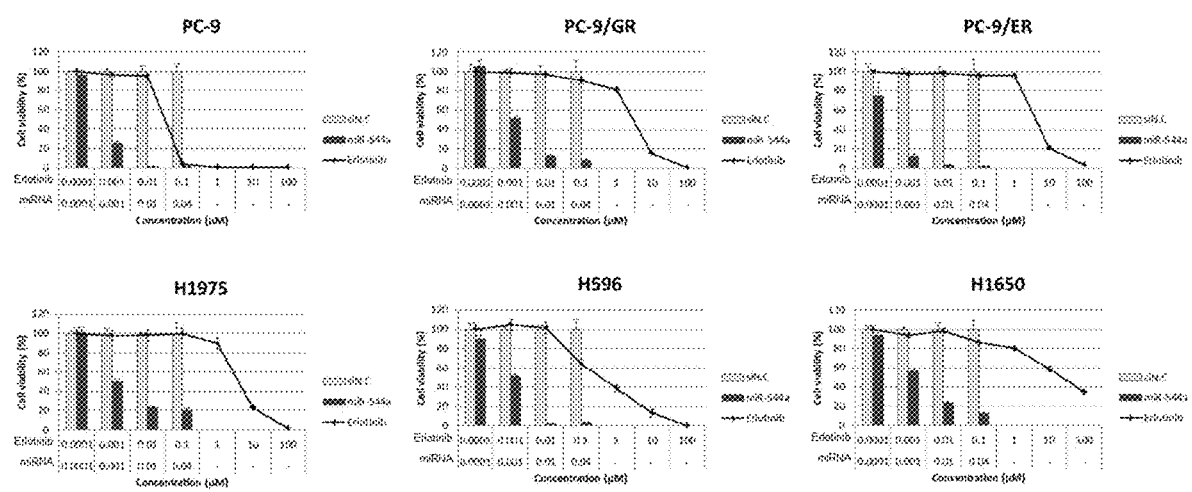

In the present invention, lung cancer cell lines having EGFR mutation were treated with a screening library of about 1,700 miRNAs and the ability to inhibit cancer cell growth was measured. As a result, miR-544a having the nucleotide sequence described below was discovered (FIGS. 1 to 4), and it was found that miR-544a had excellent anticancer efficacy (FIGS. 5, 6 and 9).

Therefore, in one aspect, the present invention is directed to a double-stranded oligonucleotide structure, which comprises miR-544a and comprises a structure of the following structural formula (1):

 (1)

In the structural formula (1), A represents a hydrophilic compound; B represents a hydrophobic compound; X and Y each independently represent a simple covalent bond or a linker-mediated covalent bond; and R represents an miR-544a sequence.

In the present invention, the miR-544a may be a double-stranded RNA, DNA or RNA-DNA hybrid consisting of the nucleotide sequences of SEQ ID NOs: 1 and 2.

```
miR-544a
                                        (SEQ ID NO: 1)
5'-AUUCUGCAUUUUUAGCAAGUUC-3'

(SEQ ID NO: 2)
5'-ACUUGCUAAAAAUGCAGAAUUU-3'
```

As described in the above "Background Art" section, the seed sequence corresponding to 8-9$^{th}$ nucleotides counting from the second nucleotide of the active sequence of miRNA is the major factor of activity. A long double-stranded sequence comprising the seed region may be used in production of the double-stranded oligonucleotide.

In the present invention, the miRNA discovered by library screening exhibited anticancer efficacy by inhibiting the EGFR signaling pathway in lung cancer cell lines having EGFR mutation.

This miRNA may comprise a duplex or single-stranded molecule polynucleotide, and may be an antisense oligonucleotide or microRNA (miRNA), but is not limited thereto.

In the case of an oligo conjugate in which a hydrophilic compound and a hydrophobic compound are bound to an RNA or DNA oligonucleotide as described in the present invention, the oligonucleotide can be efficiently delivered in vivo and the stability thereof can also be improved, through the conjugate in which the hydrophilic compound and the hydrophobic compound are conjugated to both ends of the RNA or DNA oligonucleotide.

Self-assembled nanoparticles are formed by the hydrophobic interaction of the hydrophobic compound moieties. These nanoparticles have advantages in that they have excellent in vivo delivery efficiency and in vivo stability, and have a very uniform particle size by improving the structure thereof, which makes quality control (QC) easy, and a process of preparing the same as drugs is simple.

In one embodiment, A representing the hydrophilic compound in the double-stranded oligonucleotide structure comprising miRNA according to the present invention is represented by $(P)_n$, $(P_m J)_n$ or $(J-P_m)_n$, wherein P may be a hydrophilic monomer; n may be 1 to 200; m may be 1 to 15; and J may be a linker that connects between m hydrophilic monomers or between m hydrophilic monomers and the oligonucleotide.

When the hydrophilic material is A, the double-stranded oligonucleotide structure according to the present invention has the following structural formula (1'):

(1')

In the structural formula (1') A, B, X and Y are as defined in structural formula (1) above, S represents the sense strand of the miRNA, and AS represents the antisense strand of the miRNA.

In one embodiment, the double-stranded oligonucleotide structure comprising miRNA according to the present invention may be a double-stranded oligonucleotide structure comprising a structure of the following structural formula (2):

A-X-5'R3'Y—B     (2)

In the structural formula (2), A, B, X, Y and R are as defined in structural formula (1) above.

More preferably, the double-stranded oligonucleotide structure has a structure of the following structural formula (2'):

(2')

In one embodiment, the hydrophilic compound may be a cationic or nonionic polymer compound having a molecular weight of 200 to 10,000, preferably a nonionic polymer compound having a molecular weight of 1,000 to 2,000. As the hydrophilic compound, a nonionic hydrophilic polymer compound, for example, polyethylene glycol, polyvinyl pyrrolidone or polyoxazoline, is preferably used, without being limited thereto.

In other embodiments, when the hydrophilic compound is $(P_m-J)_n$ or $(J-P_m)_n$, the double-stranded oligonucleotide structure according to the present invention has a structure of the following structural formula (3) or (4):

(3)

(4)

In the structural formula (3) and (4), P may be a hydrophilic monomer; n may be 1 to 200; m may be 1 to 15; J may be a linker that connects between m hydrophilic monomers or between m hydrophilic monomers and the oligonucleotide; X and Y may be each independently a simple covalent bond or a linker-mediated covalent bond; and R may be the specific miRNA of the present invention. More preferably, the double-stranded oligonucleotide comprising miRNA according to the present invention has a structure of the following structural formula (3'):

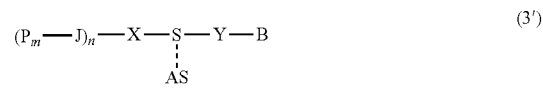
(3')

In the structural formula (3'), P, B, J, m, n, X and Y are as defined in structural formula (3) above, S represents the sense strand of the miRNA, and AS represents the antisense strand of the miRNA.

More preferably, the double-stranded oligonucleotide structure comprising miRNA according to the present invention has a structure of the following structural formula (4'):

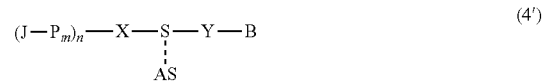
(4')

In the structural formula (4'), P, B, J, m, n, X and Y are as defined in structural formula (4) above, S represents the sense strand of the miRNA, and AS represents the antisense strand of the miRNA.

As the hydrophilic monomer (P) in structural formula (3) and structural formula (4) above, any one selected from among nonionic hydrophilic monomers may be used without limitation as long as it satisfies the purpose of the present invention. Preferably, it is possible to use a monomer selected from among compounds (1) to (3) shown in Table 1 below, more preferably a monomer of compound (1). G in compound (1) may preferably be selected from among $CH_2$, O, S and NH.

In particular, among hydrophilic monomers, the monomer represented by compound (1) has advantages in that it may have excellent biocompatibility such as being introduced with various functional groups, having excellent bioaffinity, inducing less immune response, and can increase the in vivo stability and delivery efficiency of the oligonucleotide contained in the structure according to structural formula (3) or structural formula (4). Due to these advantages, the monomer is very suitable for production of the structure according to the present invention.

TABLE 1

Preferred hydrophilic monomer structures in the present invention

| Compound (1) | Compound (2) | Compound (3) |
|---|---|---|
| 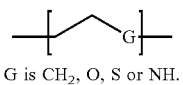 G is $CH_2$, O, S or NH. | 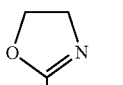 | 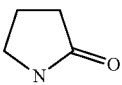 |

The total molecular weight of the hydrophilic compound in structural formula (3) or structural formula (4) is preferably in the range of 1,000 to 2,000. Thus, for example, when the hexa(ethylene glycol) of compound (1) is used, that is, when a compound, in which G in structural formula (3) or structural formula (4) is O and m is 6, is used, the repeat number (n) is preferably 3 to because the hexa(ethylene glycol) spacer has a molecular weight of 344.

The present invention is characterized in that a suitable number (represented by n) of repeat units of the hydrophilic group (hydrophilic blocks) represented by ($P_m$-J) or (J-$P_m$) in structural formula (3) or structural formula (4) may be used as required. The hydrophilic monomer P and linker J included in each hydrophilic block may be the same or different between the hydrophilic blocks. In other words, when 3 hydrophilic blocks are used (n=3), the hydrophilic monomer of compound (1), the hydrophilic monomer of compound (2) and the hydrophilic monomer of compound (3) may be used in the first, second and third blocks, respectively, suggesting that different monomers may be used in all hydrophilic blocks. Alternatively, any one selected from the hydrophilic monomers of compounds (1) to (3) may also be used in all the hydrophilic blocks. Similarly, as the linker that mediates bonding of the hydrophilic monomer, the same linker may be used in all hydrophilic blocks, or different linkers may be used in the hydrophilic blocks. In addition, m, which is the number of the hydrophilic monomers, may also be the same or different between the hydrophilic blocks. In other words, in the first hydrophilic block, three hydrophilic monomers are connected (m=3), and in the second hydrophilic block, five hydrophilic monomers are connected (m=5), and in the third hydrophilic block, four hydrophilic monomers are connected (m=4), suggesting that different numbers of the hydrophilic monomers may be used in the hydrophilic blocks. Alternatively, the same number of the hydrophilic monomers may also be used in all the hydrophilic blocks.

In addition, in the present invention, the linker (J) is preferably selected from the group consisting of $PO_3^-$, $SO_3$ and $CO_2$, but is not limited thereto. It will be obvious to those skilled in the art that any linker selected depending on the hydrophilic monomer used may be used, as long as it satisfies the purpose of the present invention.

All or part of the hydrophilic material monomer may be modified to have a functional group necessary for binding to other materials, such as a target specific ligand, as necessary.

In some cases, one to three phosphate groups may be bound to the 5' end of the antisense strand of the double-stranded oligonucleotide structure comprising the gene-specific miRNA.

For example, the double-stranded oligonucleotide structure comprising the miRNA may have a structure of the following structural formula (3') or structural formula (4'):

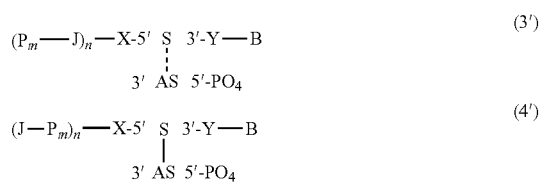

The hydrophobic compound (B) serves to form nanoparticles consisting of the oligonucleotide of structural formula (1) by hydrophobic interaction.

The hydrophobic compound preferably has a molecular weight of 250 to 1,000, and may be selected from among a steroid derivative, a glyceride derivative, glycerol ether, polypropylene glycol, a $C_{12}$ to $C_{50}$ unsaturated or saturated hydrocarbon, diacylphosphatidylcholine, fatty acid, phospholipid, lipopolyamine or the like, but is not limited thereto. It will be obvious to those skilled in the art that any hydrophobic compound may be used as long as it satisfies the purpose of the present invention.

The steroid derivative may be selected from the group consisting of cholesterol, cholestanol, cholic acid, cholesteryl formate, cholestanyl formate, and cholesteryl amine, and the glyceride derivative may be selected from among mono-, di-, and tri-glycerides. Here, fatty acid of the glyceride is preferably $C_{12}$-$C_{50}$ unsaturated or saturated fatty acid.

In particular, among the hydrophobic compounds, the saturated or unsaturated hydrocarbon or cholesterol is preferably used, because it has an advantage of that it can be easily bound in a process of synthesizing the oligonucleotide structure according to the present invention.

The hydrophobic compound may be bound to the opposite end to the hydrophilic compound, and may be bound to any position of the sense or antisense strand of the miRNA.

In the present invention, the hydrophilic compound, the hydrophilic compound block or the hydrophobic compound is bound to the oligonucleotide by a single covalent bond or a linker-mediated covalent (X or Y). The covalent bond may be any one of a non-degradable bond and a degradable bond. Here, examples of the non-degradable bond include, but are not limited to, an amide bond and a phosphate bond, and examples of the degradable bond include, but are not limited to, a disulfide bond, an acid-degradable bond, an ester bond, an anhydride bond, a biodegradable bond, and an enzyme-degradable bond.

In other examples of the present invention, the miRNA oligonucleotide structure according to the present invention was produced, lung cancer cell lines were treated with the produced oligonucleotide structure, and the cell lines were stained with Annexin V and analyzed by flow cytometry. As a result, as shown in FIG. 9, it could be confirmed that, when nanoparticles consisting of the miRNA structure were used to increase stability in vivo, apoptosis of the cell lines could be induced dependently in a concentration-dependent manner.

Therefore, in another aspect, the present invention is directed to a composition for cancer prevention or treatment. The present invention is also directed to a method for cancer prevention or treatment comprising a step of administering the oligonucleotide structure. The present invention also provides the oligonucleotide structure for use in cancer prevention or treatment. The present invention also provides the use of the oligonucleotide structure in the manufacture of a medicament for cancer prevention or treatment.

In the present invention, the cancer may be one or more cancers selected from the group consisting of a primary cancer such as lung cancer, liver cancer, stomach cancer, colorectal cancer, pancreatic cancer, gallbladder and bile duct cancer, breast cancer, leukemia, esophageal cancer, non-Hodgkin's lymphoma, thyroid cancer, cervical cancer, or skin cancer; a metastatic carcinoma arising from metastasis to other organs from the primary cancer site of origin; and a neoplastic cell disease caused by the promotion of abnormally excessive cell division, but is not limited thereto.

The sequence of miRNA that may be used as an active ingredient of the pharmaceutical composition for cancer treatment according to the present invention is a sequence derived from the human genome, but may be a miRNA sequence obtained from other animal genomes without limiting the miRNA-derived genome to the human genome.

The miRNA may be used as various miRNA mimics, which generate biologically equivalent effect. For example, modified miRNA comprising a miRNA sequence containing the same seed region may be used. Here, the length of SEQ ID NO: 1 or SEQ ID NO: 2 may be reduced, and a short-length miRNA mimic consisting of 15 nucleotides may also be used.

miRNA mimics for the miRNA may partially comprise a phosphorothioate structure in which an RNA phosphate backbone structure is substituted with another element such as sulfur. Moreover, those obtained by wholly or partially substituting RNA with a DNA, PNA (peptide nucleic acid) or LNA (locked nucleic acid) molecule may also be used. In addition, those obtained by substituting the 2' hydroxyl group of RNA sugar with various functional structures including methylation, methoxylation, fluorination or the like may also be used, but is not limited to.

The miRNA is not limited to the mature miRNA and the double-stranded RNA of the miRNA mimic derived therefrom, but may be used in the form of a miRNA precursor. The miRNA precursor may also be obtained by substitution of the above-described RNA phosphate backbone structure, whole or partial substitution of RNA nucleic acid with DNA, PNA or LNA, or modification of the 2' hydroxyl group of RNA sugar.

The miRNA may be used in the form of a miRNA precursor or primary miRNA (pri-miRNA), and can be synthesized by a chemical method or delivered to cells in the form of a plasmid so as to be expressed.

Examples of a method of delivering the miRNA to cells cultured in a culture dish, which may be used in the present invention, include, but are not limited to, a method of using a mixture of miRNA and a cationic lipid, a method of delivering the miRNA to cells by electrical stimulus, and a method of using a virus.

The composition for cancer treatment comprising the miRNA as an active ingredient may be a pharmaceutical composition further comprising a pharmaceutically acceptable carrier, and may be formulated together with the carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, as a sterile and biocompatible carrier, physiological saline, sterile water, Ringer's solution, buffered saline, albumin injection solution, dextrose solution, maltodextrin solution, glycerol, ethanol, or a mixture of two or more thereof may be used. In addition, the composition of the present invention may, if necessary, comprise other conventional additives, including antioxidants, buffers, and bacteriostatic agents. Furthermore, the composition of the present invention may be formulated as injectable forms such as aqueous solutions, suspensions or emulsions, pills, capsules, granules, or tablets with the aid of diluents, dispersants, surfactants, binders and lubricants.

The composition for cancer prevention or treatment, which comprises the miRNA and a pharmaceutically acceptable carrier, can be applied as any formulation comprising the same as an active ingredient and may be prepared as an oral or parenteral formulation. Pharmaceutical formulations of the present invention include those suitable for oral, rectal, nasal, topical (including buccal and sublingual), subcutaneous, vaginal or parenteral (including intramuscular, subcutaneous and intravenous) administration or a form suitable for administration by inhalation or insufflation.

Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may comprise a binder such as lactose, saccharose, sorbitol, mannitol, starch, amylopectin, cellulose or gelatin, an excipient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas containing conventional suppository bases such as cocoa butter or other glycerides. For spray formulations, such as aerosols, a propellant for spraying a water-dispersed concentrate or wet powder may be used in combination with an additive.

EXAMPLES

Hereinafter, the present invention will be described in more detail with reference to examples. It will be obvious to skilled in the art that these examples are merely to illustrate the present invention, and the scope of the present invention is not limited by these examples.

Example 1: miRNA Screening Using miRNA Library

Using the same miRNA library used in Korean Patent Application No. 10-2016-0022462, an experiment was performed to screen miRNAs that induce apoptosis of lung cancer cell lines. The lung cancer cell lines used in the experiment are as follows: H2009, H596, H1650, PC9, PC9/GR, H1975, HCC827, and A549 (purchased from the ATCC or the Korean Cell Line Bank). Each of the cell lines was seeded into a 96-well plate and treated with 40 nM of each miRNA together with the transfection reagent RNAiMax (Invitrogen), and the miRNA was delivered into the cells. After 96 hours of additional culture, the relative growth of the cells was measured using CellTiter-Glo reagent (Promega) (FIGS. 1 to 4). Among the miRNAs, miR-544a was selected as a miRNA having an excellent effect against the cell lines used.

Example 2: Analysis of Apoptotic Effect of miRNA

The experiment performed in Example 1 was performed by a method of measuring the inhibitory effect of miRNA on cell proliferation. Methods capable of inhibiting cell proliferation can be broadly divided into two: one is a method of preventing the transition from a specific stage to the next stage in the cell cycle, and the other is a method for inducing apoptosis.

In order to examine how the miRNA selected in Example 1 exhibits a cell proliferation inhibitory effect, an experiment was performed on the PC9 and PC9/ER cell lines. Each of the cell lines was seeded and cultured in a 6-well plate, and then each of a miRNA control and miR-544a was delivered into cells using the transfection reagent RNAiMax (Invitrogen) to reach a concentration of nM. After 48 hours of additional culture, the cells were treated with FITC fluorescent dye-labeled annexin V and propidium iodide (PI) and analyzed by flow cytometry (FACS). As a result, it was confirmed that the number of dead cells in the cell line treated with miR-544a was significantly higher than that in the cell line treated with the miRNA control. This suggests that miR-544a exhibits a cell proliferation inhibitory effect by inducing apoptosis (FIG. 5).

Example 3: Analysis of Mechanism by which miR-544a Induces Apoptosis

In order to examine the mechanism by which miR-544a identified in Examples 1 and 2 induces apoptosis of the lung cancer cell lines, the effects of miR-544a on the signaling pathway in the cell lines used were measured. It is known that the EGFR signaling pathway in the lung cancer cell lines used in the Examples is activated due to the presence of mutation in the EGFR protein and activation of the EGFR signaling pathway plays an important role in the survival of the cell lines.

Thus, since the mechanism by which miR-544a induces apoptosis of the cell lines was predicted to regulate the EGFR signaling pathway, the expression levels of the proteins involved in the EGFR signaling pathway were measured by Western blot analysis. The results of the measurement are shown in FIG. 6. It can be seen that the expression level of the EGFR protein in the sample treated with miR-544a significantly decreased compared to that in the control group, and the expression level of phosphorylated EGFR, indicative of the activity of the EGFR protein, also decreased compared to that in the control group.

The ERK signaling pathway is located downstream of the EGFR signaling pathway, and it could be confirmed that, because the EGFR signaling pathway was inhibited by miR-544a, the amount of ERK, an activated form of the ERK protein, decreased (FIG. 6).

Example 4: Confirmation that miR-544a Inhibits Expression of EGFR mRNA

It is known that, when the expression of protein is decreased by miRNA as indicated by the data shown in FIG. 6, the expression of mRNA is also generally inhibited by miRNA. To confirm this fact, the lung cancer cell lines PC9, PC9/ER, H1975 and H596 were treated with miR-544a or a negative control, and then the relative expression level of EGFR mRNA was analyzed.

Figure 7:
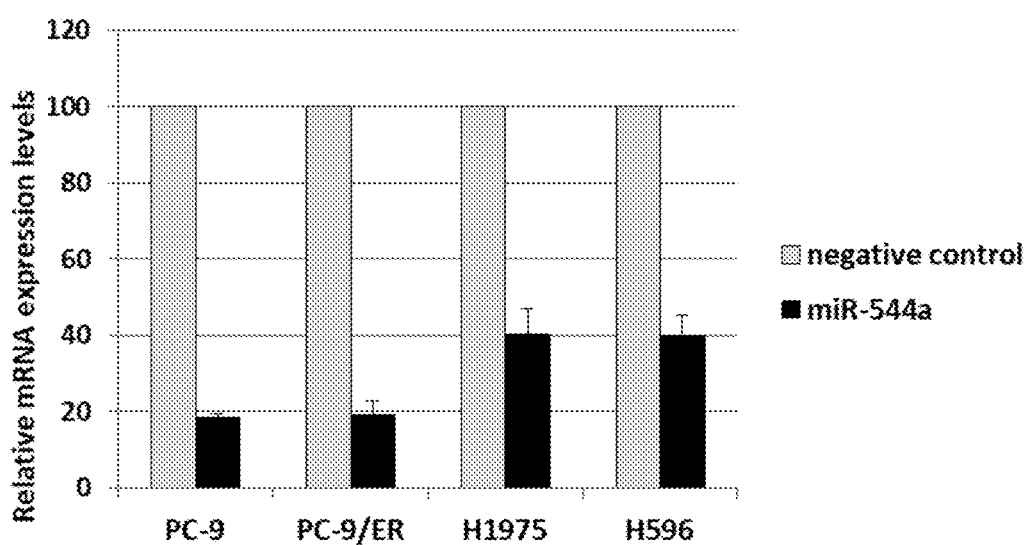
FIG. 7 shows the results of RT-qPCR assay performed to analyze the effect of miR-544a on the inhibition of EGFR mRNA in the PC9, PC9/ER, H1975 and H596 cell lines.

As a result, it could be confirmed that the expression of EGFR mRNA decreased in all the cell lines used in the experiment (FIG. 7).

Example 5: Identification of Direct Target mRNA of miR-544a by Luciferase Assay

Since miRNA inhibits protein production from target mRNA by binding to the 3' UTR (untranslated region) of the target mRNA, luciferase assay is generally used as a method of directly measuring the relationship between miRNA and the target mRNA. Using the TargetScan software, a 3' UTR sequence comprising a miRNA binding sequence was predicted. The predicted 3' UTR sequence was cloned into the 3' UTR of firefly luciferase by a gene cloning technique. The constructed vector and the miRNA of interest were co-transfected into human embryonic kidney (HEK) cells, and the luciferase expression level of the vector was measured. To examine whether EGFR mRNA becomes a target of miR-544a, the 3' UTR of EGFR mRNA was divided into a and b and inserted into the firefly luciferase vector. At this time, in order to correct the transfection efficiency, *Renilla* luciferase was also transfected to correct the measurement value. After co-transfection of the miRNA, firefly luciferase and *Renilla* luciferase, the cells were cultured for 48 hours, and then the luciferase activity was measured using a luminometer.

Figure 8:
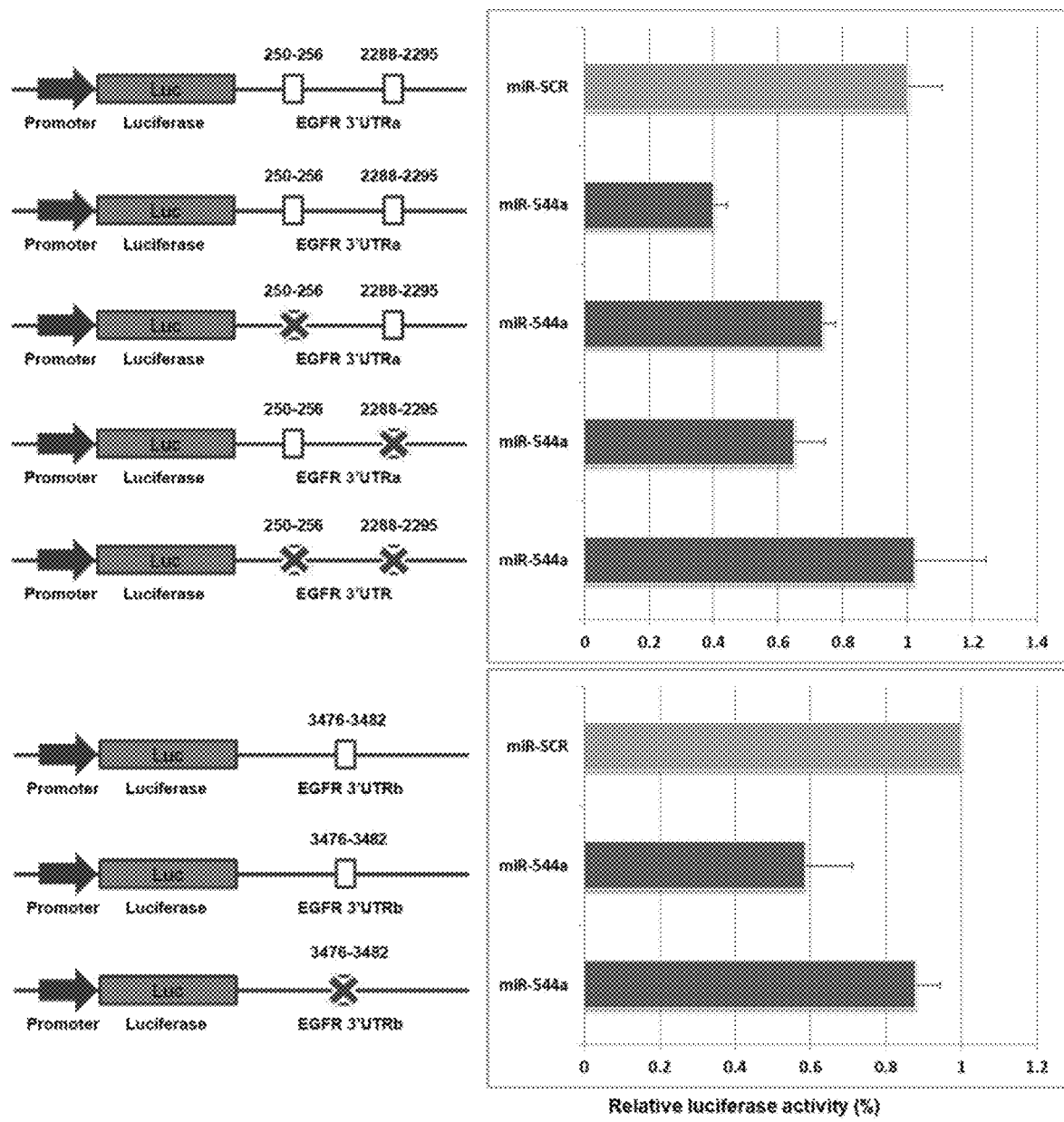
FIG. 8 shows the results of verifying a target sequence of miR-544a by luciferase assay and indicates that, when the target sequence is removed from the EGFR 3'UTR sequence, the inhibition of luciferase activity by miR-544a disappears.

As a result, as shown in FIG. 8, it could be confirmed that each target mRNA was controlled directly by the miRNA. In addition, it was confirmed that, when the sequences of the EGFR 3'UTR, on which the miRNA acts, were predicted and mutations (EGFR 3'UTR 250-256, 2288-2295, and 3476-3482 nt) in the corresponding regions were induced, the expression inhibition phenomenon by the miRNA disappeared. Thus, it was confirmed that the miRNA controls the target mRNA by direct binding to the regions on which it acts.

Example 6: Evaluation of Whether miR-544a Overcomes Drug Resistance

The efficacy of erlotinib, which is clinically used as a therapeutic agent for lung cancer having EGFR mutation, was evaluated comparatively with that of miR-544a. The cell lines having EGFR mutation, PC9, PC9/GR, PC9/ER, H1975, H596 and H1650, were seeded and cultured in 96-well plates, and then treated with erlotinib at the concentrations shown in FIG. 9. After 96 hours of additional culture, the relative viability of the cells was measured. These cell lines were used because they have genetic characteristics and drug resistance as follows. PC9 contains delE764-A750 mutation and has excellent sensitivity to erlotinib, and thus when PC9 is treated with erlotinib, it can be effectively killed. On the other hand, PC9/GR and PC9/ER contain delE764-A750 mutation, like PC9, and have T790M mutation. For this reason, they are cell lines having resistance to erlotinib. H1975 has L858R and T790M mutations, H596 has overexpressed EGFR, and H1650 has delE764-A750 mutation. These cell lines are all cell lines having resistance to erlotinib. The cell viability was measured using the CellTiter-Glo used in Example 1. Similarly, the cell lines were treated with each of the miR control and miR-544a at the concentrations shown in FIG. 9 together with the RNAiMax transfection reagent, and the relative viability of the cells was measured under the same conditions as those for the erlotinib-treated group.

As a result, as shown in FIG. 9, it was confirmed that the PC9 cell line known to be highly sensitive to erlotinib could be killed by erlotinib at a concentration of 0.1 μM, but when the other cell lines having resistance to erlotinib due to mutations such as EGFR T790M were treated with erlotinib at a concentration of 10 μM which is 100-fold higher than that for the PC9 cell line, apoptosis of the cells could be induced. On the other hand, it was confirmed that miR-544a could induce apoptosis of the cells at a treatment concentration of 0.001 to 0.01 μM regardless of the presence of EGFR T790M mutation.

This suggests that the miRNA is effective at a lower concentration than erlotinib and can effectively act regardless of erlotinib resistance caused by EGFR T790M mutation. In addition, the same results could also be confirmed from the Western blot results shown in FIG. 6. In the PC9 cell line, miR-544a and erlotinib inhibit activated EGFR (pEGFR) and inhibit phosphorylation of the downstream signaling factor ERK. As a result, they induce apoptosis as can be seen from PARP. However, in the other cell lines having erlotinib resistance due to EGFR T790M mutation, only miR-544a exhibits this effect.

Example 7: Synthesis of RNA Oligonucleotide Structure

The double-stranded oligonucleotide structure produced in the present invention has a structure represented by the following structural formula (5):

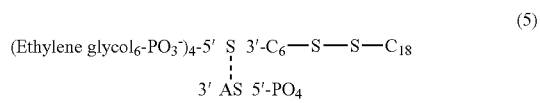

(5)

In structural formula (5) above, S represents the sense strand of the miRNA; AS represents the antisense strand of the miRNA; $PO_4$ is a phosphate group; the ethylene glycol is a hydrophilic monomer, and the hexa(ethylene glycol) is bonded via the linker (J) phosphate group ($PO_3^-$); $C_{24}$ is tetradocosane which is a hydrophobic compound containing a disulfide bond; and 5' and 3' refer to the directions of the ends of the double-stranded oligo RNA.

The sense strand of the miRNA in structural formula (5) above was synthesized as follows. Using DMT-hexa(ethylene glycol)-CPG as a support and β-cyanoethyl phosphoramidite, an oligonucleotide-hydrophilic compound structure comprising a sense strand having hexa(ethylene glycol) bonded to the 3' end was synthesized by a method of connecting a phosphodiester bond forming an oligonucleotide framework structure. Then, tetradocosane containing a disulfide bond was bonded to the 5' end, thus preparing the sense strand of the desired oligonucleotide-polymer structure. In the case of the antisense strand to be annealed to the sense strand, the antisense strand having a sequence complementary to the sense strand was prepared through the above-mentioned reaction.

Example 8: Induction of Apoptosis by Oligonucleotide Structure Comprising miRNA Sequence To ensure the in vivo stability of the miRNA screened through the above Examples, an oligonucleotide structure was produced according to the method of Example 7. In order to evaluate whether the produced nanoparticles also induce apoptosis of lung cancer cell lines, the lung cancer cell lines A549 and H1650 were seeded and cultured in 96-well plates, and the nanoparticles were added to media at a concentration of 1000 nM. The cells were cultured in the media containing the nanoparticles, and then the relative growth of the cells was measured using CellTiter-Glo reagent (Promega).

Figure 10:
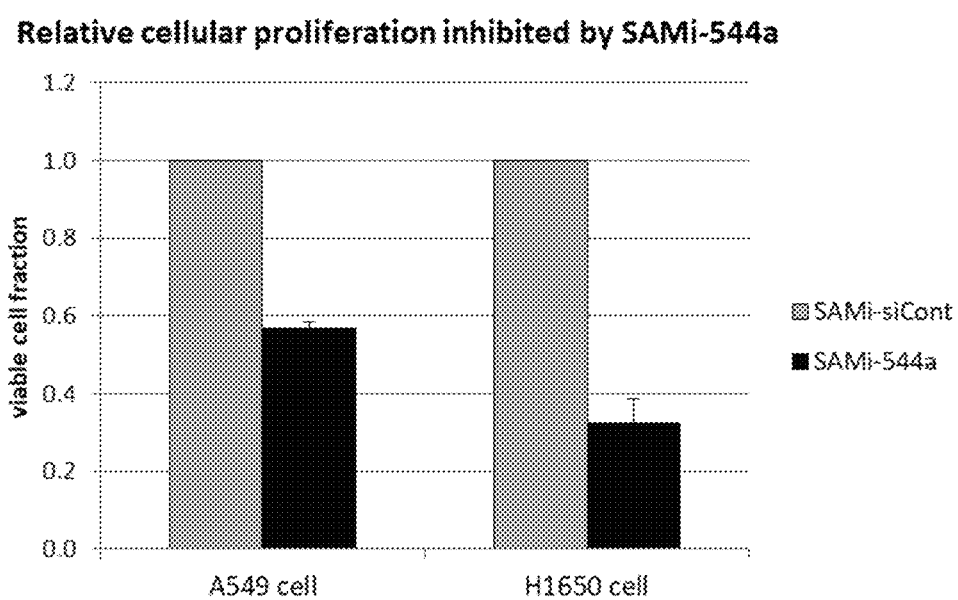
FIG. 10 shows the effect of a miRNA, prepared as an oligonucleotide structure, on the apoptosis of lung cancer cell lines.

As a result, it was confirmed that apoptosis was induced by the miRNA prepared as the oligonucleotide structure (FIG. 10).

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

The double-stranded oligonucleotide structure according to the present invention and a composition for cancer treatment comprising the same comprise miR-544a which exhibits an improved anticancer effect compared to the drug erlotinib that is clinically used for lung cancer having EGFR mutation. Thus, the double-stranded oligonucleotide structure and the composition may be widely used as an anticancer therapeutic agent.

SEQUENCE LIST FREE TEXT

Electronic file is attached.

The invention claimed is:

1. A method for treatment of lung cancer by inhibiting EGF signaling comprising administering a double-stranded oligonucleotide structure comprising a structure of the following structural formula (1):

$$A-X-R-Y-B \quad (1)$$

wherein A represents a hydrophilic compound; B represents a hydrophobic compound; X and Y each independently represent a simple covalent bond or a linker-mediated covalent bond; and R represents miR-544a.

2. The method of claim 1, wherein the hydrophilic compound A is represented by $(P)_n$, $(P_m\text{-}J)$ or $(J\text{-}P_m)_n$, wherein P is a hydrophilic monomer, n is 1 to 200, m is 1 to 15, and J is a linker that connects between m hydrophilic monomers or between m hydrophilic monomers and the oligonucleotide.

3. The method of claim 2, wherein the hydrophilic compound has a molecular weight of 200 to 10,000.

4. The method of claim 2, wherein the hydrophilic monomer (P) has a structure of the following compound (1):

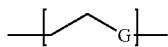

compound (1)

wherein G is selected from the group consisting of $CH_2$, O, S and NH.

5. The method of claim 2, wherein the linker (J) is selected from the group consisting of $PO_3^-$, $SO_3$ and $CO_2$.

6. The method of claim 2, wherein the hydrophobic compound has a molecular weight of 250 to 1,000.

7. The method of claim 6, wherein the hydrophobic compound is selected from the group consisting of a steroid derivative, a glyceride derivative, glycerol ether, polypropylene glycol, a $C_{12}$-$C_{50}$ unsaturated or saturated hydrocarbon, diacylphosphatidylcholine, fatty acid, phospholipid, and lipopolyamine.

8. The method of claim 7, wherein the steroid derivative is selected from the group consisting of cholesterol, cholestanol, cholic acid, cholesteryl formate, cholestanyl formate, and cholesteryl amine.

9. The method of claim 7, wherein the glyceride derivative is selected from among mono-, di-, and tri-glycerides.

10. The method of claim 1, wherein the covalent bond represented by each of X or Y is a non-degradable bond or a degradable bond.

11. The method of claim 10, wherein the non-degradable bond is an amide bond or a phosphate bond.

12. The method of claim 10, wherein the degradable bond is a disulfide bond, an acid-degradable bond, an ester bond, an anhydride bond, a biodegradable bond, or an enzyme-degradable bond.

13. The method of claim 1, wherein the miR-544a comprises, as an active ingredient, a double strand composed of a double-stranded RNA consisting of the nucleotide sequences of SEQ ID NO: 1 and SEQ ID NO: 2.

14. The method of claim 1, wherein the oligonucleotide treats lung cancer by inducing lung cancer cell apoptosis.

* * * * *

UNITED STATES PATENT AND TRADEMARK OFFICE
CERTIFICATE OF CORRECTION

| | | |
|---|---|---|
| PATENT NO. | : 11,820,984 B2 | Page 1 of 1 |
| APPLICATION NO. | : 16/963998 | |
| DATED | : November 21, 2023 | |
| INVENTOR(S) | : Lee et al. | |

It is certified that error appears in the above-identified patent and that said Letters Patent is hereby corrected as shown below:

In the Specification

Column 3, Line 38, "(UnTranslated Region)" should be -- (Un-Translated Region) --.

Column 7, Line 27, "$(P_mJ)_n$" should be -- $(P_m\text{-}J)_n$ --.

Column 13, Line 19, "nM" should be -- 40 nM --.

In the Claims

Column 17, Line 24, "$(P_m\text{-}J)$" should be -- $(P_m\text{-}J)_n$ --.

Signed and Sealed this
Twenty-third Day of January, 2024

*Katherine Kelly Vidal*

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: miR-544a_5'

<400> SEQUENCE: 1
auucugcauu uuuagcaagu uc                    22

<210> SEQ ID NO 2

```
<211> LENGTH: 22
<212> TYPE: RNA
<213> ORGANISM: Artificial Sequence
<220> FEATURE:
<223> OTHER INFORMATION: miR-544a_3'

<400> SEQUENCE: 2
acuugcuaaa aaugcagaau uu                                               22
```